United States Patent
Morimoto et al.

(10) Patent No.: US 10,472,593 B2
(45) Date of Patent: Nov. 12, 2019

(54) LIQUID DETERGENT

(71) Applicant: LION CORPORATION, Tokyo (JP)

(72) Inventors: Yuka Morimoto, Tokyo (JP); Takayasu Kubozono, Tokyo (JP); Akinori Joko, Tokyo (JP); Atsunori Morigaki, Tokyo (JP)

(73) Assignee: Lion Corporation, Tokyo (JP)

( * ) Notice: Subject to any disclaimer, the term of this patent is extended or adjusted under 35 U.S.C. 154(b) by 0 days.

(21) Appl. No.: 15/743,653

(22) PCT Filed: Jul. 28, 2016

(86) PCT No.: PCT/JP2016/072176
§ 371 (c)(1),
(2) Date: Jan. 10, 2018

(87) PCT Pub. No.: WO2017/022624
PCT Pub. Date: Feb. 9, 2017

(65) Prior Publication Data
US 2018/0265807 A1    Sep. 20, 2018

(30) Foreign Application Priority Data
Jul. 31, 2015 (JP) .................. 2015-152134

(51) Int. Cl.

| | |
|---|---|
| *C11D 1/02* | (2006.01) |
| *C11D 1/72* | (2006.01) |
| *C11D 1/74* | (2006.01) |
| *A61K 8/39* | (2006.01) |
| *A61Q 5/02* | (2006.01) |
| *A61Q 19/10* | (2006.01) |
| *C11D 1/22* | (2006.01) |
| *C11D 1/28* | (2006.01) |
| *C11D 1/29* | (2006.01) |
| *C11D 17/08* | (2006.01) |
| *A61K 8/46* | (2006.01) |
| *A61K 8/86* | (2006.01) |
| *C11D 1/83* | (2006.01) |
| *C11D 3/00* | (2006.01) |

(52) U.S. Cl.
CPC .................. *C11D 1/74* (2013.01); *A61K 8/39* (2013.01); *A61K 8/463* (2013.01); *A61K 8/466* (2013.01); *A61K 8/86* (2013.01); *A61Q 5/02* (2013.01); *A61Q 19/10* (2013.01); *C11D 1/22* (2013.01); *C11D 1/28* (2013.01); *C11D 1/29* (2013.01); *C11D 1/83* (2013.01); *C11D 3/0036* (2013.01); *C11D 17/08* (2013.01); *A61K 2800/596* (2013.01)

(58) Field of Classification Search
CPC ................ C11D 1/02; C11D 1/72; C11D 1/74
See application file for complete search history.

(56) References Cited

U.S. PATENT DOCUMENTS

2014/0187466 A1 *    7/2014   Lin .......................... C11D 1/83
                                                            510/340

FOREIGN PATENT DOCUMENTS

| GB | 2523951 | | 9/2015 | |
|---|---|---|---|---|
| JP | 10-001696 | | 1/1998 | |
| JP | 11-505839 | | 5/1999 | |
| JP | 2003-171700 | | 6/2003 | |
| JP | 2007-177101 | | 7/2007 | |
| JP | 2009-161591 | * | 7/2009 | ............... C11D 1/72 |
| JP | 2009-191128 | | 8/2009 | |
| JP | 2009-263464 | | 11/2009 | |
| JP | 2012-087228 | | 5/2012 | |
| JP | 2012-224956 | | 11/2012 | |
| JP | 2015-074762 | * | 4/2015 | ............... C11D 1/74 |
| WO | 96/37589 | | 11/1996 | |
| WO | 2012/144438 | | 10/2012 | |
| WO | 2014/109380 | | 7/2014 | |

OTHER PUBLICATIONS

Japanese Patent Office, "International Search Report" in connection with related International Application No. PCT/JP2016/072176, dated Sep. 20, 2016, 5 pages.

* cited by examiner

*Primary Examiner* — Brian P Mruk
(74) *Attorney, Agent, or Firm* — Kolisch Hartwell, P.C.

(57) ABSTRACT

A liquid detergent of the present invention contains: component (a): a nonionic surfactant which contains compounds represented by the following formula (1) wherein an average value of m in formula (1) ranges from 5 to 20; and in which a ratio of the compound wherein $R^1$ is a double bond-containing unsaturated hydrocarbon group is equal to or greater than 45% by mass with respect to a total amount of the component (a), and a ratio of the compound wherein $R^1$ is an unsaturated hydrocarbon group having two or more double bonds is equal to or greater than 4% by mass with respect to a total amount of the compounds of formula (1) wherein $R^1$ is an unsaturated hydrocarbon group; and component (b): an anionic surfactant.

$$R^1CO(EO)_mOR^2 \qquad (1)$$

wherein $R^1$ is a saturated or unsaturated hydrocarbon group having 15 to 17 carbon atoms; EO is an oxyethylene group; m is a positive integer; and $R^2$ is an alkyl group having 1 to 3 carbon atoms.

1 Claim, No Drawings

LIQUID DETERGENT

TECHNICAL FIELD

The present invention relates to a liquid detergent.
Priority is claimed on Japanese Patent Application No. 2015-152134, filed in Japan on Jul. 31, 2015, the contents of which are incorporated herein by reference.

BACKGROUND ART

When textile products such as clothes are laundered using a detergent, there is a problem with a phenomenon of soil redeposition, that is, a phenomenon in which some of the soils which have been separated from the fibers of the objects to be laundered and dispersed in the laundering liquid adhere again to the fibers. In recent years, with increased environmental awareness, water-saving type washing machines have been mainly used. During laundering in a water-saving type washing machine, a bath ratio (a ratio of the laundering liquid to the objects to be laundered such as clothes) is low, and soil redeposition tends to be problematic. In particular, in the case of using a liquid detergent containing a nonionic surfactant as the main detergent component, the negative charge on the surface of the object to be laundered is weak, and for this reason, redeposition due to carbon soils or the like is likely to occur.

In order to suppress the soil redeposition as described above, it has been proposed to combine a nonionic surfactant and an anionic surfactant in a liquid detergent (for example, Patent Document 1). However, the effect of suppressing soil redeposition is still insufficient and further improvement is required.

With respect to the aforementioned carbon soils, in recent years, there is a concern that air pollutants such as PM 2.5 adhere to clothes, and further improvement is required for detergency in addition to suppression of soil redeposition.

CITATION LIST

Patent Documents

Patent Document 1: Japanese Unexamined Patent Application, First Publication No. 2009-191128.

SUMMARY OF INVENTION

Technical Problem

The inventors of the present application focused attention on a fatty acid polyethylene alkyl ether, which is one type of a nonionic surfactant, and as a result of diligent studies, they discovered that when the number of carbon atoms of the fatty acid residue is 16 or more, a superior effect of suppressing soil redeposition can be exhibited. However, in a liquid detergent containing a fatty acid polyethylene alkyl ether having the fatty acid residue having 16 or more carbon atoms, at the time of storing it under a low-temperature environment, the liquid detergent may be solidified or precipitation may occur in some cases (poor stability at low temperature).

An object of the present invention is to provide a liquid detergent which exhibits a superior effect of suppressing redeposition of carbon soils, and has superior detergency and superior stability at low temperature.

Solution to Problem

The present invention has aspects described below.
<1> A liquid detergent, containing: component (a): a nonionic surfactant which contains compounds represented by the following formula (1) wherein an average value of m ranges from 5 to 20, and in which a ratio of the compound of formula (1) wherein $R^1$ is a double bond-containing unsaturated hydrocarbon group is equal to or greater than 45% by mass with respect to a total amount of the component (a), and a ratio of the compound wherein $R^1$ is an unsaturated hydrocarbon group having two or more double bonds is equal to or greater than 4% by mass with respect to a total amount of the compounds wherein $R^1$ is an unsaturated hydrocarbon group; and component (b): an anionic surfactant.

$$R^1CO(EO)_mOR^2 \quad (1)$$

wherein $R^1$ is a saturated or unsaturated hydrocarbon group having 15 to 17 carbon atoms; EO is an oxyethylene group; m is a positive integer; and $R^1$ is an alkyl group having 1 to 3 carbon atoms.

<2> The liquid detergent according to <1>, wherein all of the double bonds contained in $R^1$ mentioned above have a cis configuration.

<3> The liquid detergent according to <1> or <2>, wherein the aforementioned component (a) is an ethylene oxide adduct of at least one fatty acid methyl ester mixture selected from the group consisting of a fatty acid methyl ester mixture derived from a palm oil-derived fraction having 18 carbon atoms, a fatty acid methyl ester mixture derived from a palm kernel oil-derived fraction having 18 carbon atoms, and a fatty acid methyl ester mixture derived from a coconut oil-derived fraction having 18 carbon atoms.

<4> The liquid detergent according to any one of <1> to <3>, wherein the aforementioned component (b) is an anionic surfactant.

<5> The liquid detergent according to <4>, wherein the aforementioned component (b) is at least one type selected from the group consisting of a linear alkyl-benzene sulfonate, an alpha-olefin sulfonate, an alpha-sulfofatty acid alkyl ester salt, an alkylsulfate, and an alkyl ether sulfate.

<6> The liquid detergent according to <5>, wherein the aforementioned component (b) has an alkyl group having 10 to 14 carbon atoms.

<7> The liquid detergent according to any one of <1> to <6>, wherein the aforementioned component (a) is contained in an amount ranging from 5 to 30% by mass with respect to a total amount of the liquid detergent.

<8> The liquid detergent according to any one of <1> to <7>, wherein the aforementioned component (b) is contained in an amount ranging from 5 to 30% by mass with respect to a total amount of the liquid detergent.

Advantageous Effects of Invention

According to the present invention, a liquid detergent is provided which exhibits a superior effect of suppressing redeposition of carbon soils, superior detergency, and superior stability at low temperature.

DESCRIPTION OF EMBODIMENTS

A liquid detergent of the present invention contains components (a) and (b) described in detail below.
<Component (a)>
Component (a) is a nonionic surfactant represented by the following formula (1):

$$R^1CO(EO)_mOR^2 \quad (1)$$

wherein $R^1$ is a saturated or unsaturated hydrocarbon group having 15 to 17 carbon atoms; EO is an oxyethylene group; m is a positive integer; and $R^2$ is an alkyl group having 1 to 3 carbon atoms.

In the aforementioned formula (1), $R^1$ is a saturated or unsaturated hydrocarbon group having 15 to 17 carbon atoms. That is, the number of carbon atoms of the fatty acid residue which component (a) has ranges from 16 to 18. When the number of carbon atoms of $R^1$ is 15 or more, a superior effect of suppressing soil redeposition is exhibited. When the number of carbon atoms of $R^1$ is 17 or less, a superior stability of the liquid detergent at low temperature is exhibited.

The saturated or unsaturated hydrocarbon group of $R^1$ is preferably linear or branched.

An unsaturated hydrocarbon group is a hydrocarbon group containing an unsaturated bond between carbon atoms, such as a double bond and a triple bond. The number of unsaturated bonds contained in the unsaturated hydrocarbon group having 15 to 17 carbon atoms is usually 1 or more and 3 or less.

In the component (a), a ratio of the compounds in which $R^1$ in formula (1) is a double bond-containing unsaturated hydrocarbon group (hereinafter, also referred to as "ratio of the unsaturated fatty acid residue") is 45% by mass or more, preferably 55% by mass or more, and more preferably 85% by mass or more, based on the total amount of the (a) component (100% by mass). When the ratio of the unsaturated fatty acid residue is equal to or greater than the aforementioned lower limit value, superior stability of the liquid detergent at low temperature is exhibited. The upper limit of the ratio of the unsaturated fatty acid residue is not particularly limited, and is preferably 95% by mass or less from the viewpoint of productivity or availability.

For the ratio of the unsaturated fatty acid residue of component (a), the ratio of the unsaturated fatty acid residue of the fatty acid alkyl ester as a raw material can be used as it is. The ratio of the unsaturated fatty acid residue of the fatty acid alkyl ester may be a known value or a value measured by a known method such as a gas chromatograph using an HP-INNOWax column manufactured by Agilent Inc.

In addition, in the component (a), a ratio of the compound of formula (1) in which $R^1$ is an unsaturated hydrocarbon group containing two or more double bonds (hereinafter, also referred to as "ratio of the polyunsaturated fatty acid residue") is 4% by mass or more, preferably 10% by mass or more, and more preferably 20% by mass or more, based on the total amount of the compounds in which $R^1$ is an unsaturated hydrocarbon group. When the ratio of the polyunsaturated fatty acid residue is equal to or greater than the aforementioned lower limit value, superior stability of the liquid detergent at low temperature is exhibited. The upper limit of the ratio of the polyunsaturated fatty acid residue is not particularly limited, and is preferably 50% by mass or less from the viewpoint of ease of production or availability.

For the ratio of the polyunsaturated fatty acid residue of component (a), the ratio of the polyunsaturated fatty acid residue of the fatty acid alkyl ester as a raw material can be used as it is. The ratio of the polyunsaturated fatty acid residue of the fatty acid alkyl ester may be a known value or a value measured by the same measurement method as that for the aforementioned ratio of the unsaturated fatty acid residue as it is.

In component (a), all the double bonds contained in $R^1$ preferably have a cis configuration.

As the ratio of the cis configuration is increased, stability of the liquid detergent at low temperature becomes superior.

"m" is the number of moles of ethylene oxide added. The average value (the average number of moles added) of m over the component (a) ranges from 5 to 20, preferably ranges from 7 to 20, more preferably ranges from 7 to 15, and in particular, preferably ranges from 9 to 15. When the average value of m is equal to or greater than the lower limit value of the range mentioned above, superior stability at low temperature is exhibited. In addition, when "m" is present within the aforementioned range, detergency, and in particular, detergency with respect to sebum contaminants is improved, and solubility of the detergent composition is improved.

In the component (a), a narrow rate indicating a distribution ratio of the compounds (ethylene oxide adducts) which are different in the number of moles of ethylene oxide added, "m", preferably ranges from 20 to 80% by mass, and more preferably ranges from 30 to 80% by mass. As the narrow rate is increased, the enhanced detergency can be obtained. In addition, when the narrow rate is 20% by mass or more, and particularly 30% by mass or more, a liquid detergent having a reduced odor of the raw materials of the surfactant can be easily obtained, since after production of the component (a), the amount of the fatty acid alkyl ester as a raw material of the component (a) which coexists with the component (a), and the amount of the ethylene oxide adduct in which "m" of the aforementioned formula (1) is 1 or 2 are reduced. The narrow rate is obtained by the following mathematical equation (I).

$$\text{Narrow rate} = \left[ \sum_{i=n_{max}-2}^{i=n_{max}+2} Yi \right] \quad (I)$$

In the aforementioned equation (I), $n_{max}$ represents the number of moles of ethylene oxide added to the ethylene oxide adduct present in the largest amount in the whole ethylene oxide adducts.

"i" represents the number of moles of the added ethylene oxide.

Yi represents the proportion (% by mass) of the ethylene oxide adduct in which the number of moles of ethylene oxide added is "i", with respect to the whole ethylene oxide adducts.

The aforementioned narrow rate can be controlled by, for example, the method for producing the component (a) (such as raw materials or preparation conditions).

$R^2$ is an alkyl group having 1 to 3 carbon atoms, and is preferably a methyl group from the viewpoint of detergency performance.

Only one type of component (a) may be used alone, or two or more types thereof may be used in combination.

As the component (a), one obtained by a known preparation method may be used, or a commercially available product may be used.

A fatty acid polyethylene alkyl ether can be easily produced by a method in which ethylene oxide is subjected to addition-polymerization to a fatty acid alkyl ester ($R^1COOR^2$) using a surface-modified composite metal oxide catalyst (see Japanese Unexamined Patent Application, First Publication No. 2000-144179).

Preferable examples of such a surface-modified composite metal oxide catalyst include a composite metal oxide catalyst such as a magnesium oxide to which metal ions ($Al^{3+}$, $Ga^{3+}$, $In^{3+}$, $Tl^{3+}$, $Co^{3+}$, $Sc^{3+}$, $La^{3+}$, $Mn^{2+}$ or the like) are added, which is subjected to surface modification with a metal hydroxide, and a calcined product catalyst of hydrotalcite which is subjected to surface modification with a metal hydroxide and/or a metal alkoxide.

In addition, in the surface modification of the composite metal oxide catalyst, the mixing ratio of the composite metal oxide and the metal hydroxide and/or metal alkoxide is preferably set to range from 0.5 to 10 parts by mass, and more preferably set to range from 1 to 5 parts by mass, with respect to 100 parts by mass of the composite metal oxide.

Examples of the fatty acid for forming a fatty acid alkyl ester include palmitic acid (C16, F0), stearic acid (C18, F0), oleic acid (C18, F1), linoleic acid (C18, F2), linolenic acid (C18, F3) and the like. The number appended after C indicates the number of carbon atoms, and the number appended after F indicates the number of carbon-carbon double bonds contained in the fatty acid residues.

The fatty acid alkyl ester may be an alkyl ester of a fatty acid derived from natural fats and oils such as palm oil, palm kernel oil, or coconut oil, or an alkyl ester of a fatty acid derived from C16 to C18 fractions derived from the aforementioned natural fats and oils. Such a fatty acid alkyl ester is a mixture of a plurality of fatty acid alkyl esters. For example, alkyl esters of fatty acids derived from C18 fractions derived from palm oil mainly include an oleic acid alkyl ester and a linoleic acid alkyl ester, as well as include a stearic acid alkyl ester, a linolenic acid alkyl ester, and the like.

As a method for preparing the component (a), a method is preferable in which as a fatty acid alkyl ester, a mixture of fatty acid methyl esters selected from the group consisting of a mixture of methyl esters of fatty acids derived from C18 fractions derived from palm oil, a mixture of methyl esters of fatty acids derived from C18 fractions derived from palm kernel oil, and a mixture of methyl esters of fatty acids derived from C18 fractions derived from coconut oil is used, and ethylene oxide is subjected to addition polymerization thereof. That is, the component (a) is preferably an ethylene oxide adduct of the fatty acid methyl ester mixture mentioned above.

The fatty acid methyl ester mixture mentioned above contains a fatty acid methyl ester in which the fatty acid residue is a double bond-containing unsaturated fatty acid residue in an amount of 45% by mass or more, and a fatty acid methyl ester in which the fatty acid residue contains two or more double bonds in an amount of 4% by mass or more. For this reason, in the preparation method, the produced fatty acid polyoxyethylene alkyl ether has an unsaturated fatty acid residue ratio of 45% by mass or more and a polyunsaturated fatty acid residue ratio of 4% by mass or more, and the component (a) can be prepared easily at low cost.

Among the fatty acid methyl ester mixtures mentioned above, in particular, a mixture of methyl esters of fatty acids derived from C18 fractions derived from palm oil is preferable since the fatty acid methyl ester in which the fatty acid residue is an unsaturated fatty acid residue containing a double bond is contained in an amount of 85% by mass or more.

As the fatty acid methyl ester mixture, that obtained by a known preparation method may be used, or a commercially available product may be used.

<Component (b)>

The component (b) is an anionic surfactant. The liquid detergent of the present invention contains the component (b) together with the component (a), and thereby, the liquid detergent exhibits superior effects of suppressing soil redeposition.

As the component (b), a known anionic surfactant can be used. Examples thereof include, for example, linear alkylbenzene sulfonic acid salts; alkyl sulfuric acid salt; alkyl ether sulfuric acid salts or alkenyl ether sulfuric acid salts; alpha-olefin sulfonic acid salts; alkane sulfonic acid salts; alpha-sulfofatty acid alkyl ester salts; carboxylic acid-type anionic surfactants such as higher fatty acid salts (soap) having 8 to 24 carbon atom, alkyl ether carboxylic acid salts, polyoxyalkylene ether carboxylic acid salts, alkyl (or alkenyl) amido ether carboxylic acid salts, and acylaminocarboxylic acid salts; phosphoric ester-type anionic surfactants such as alkyl phosphoric ester salts, polyoxyalkylene alkyl phosphoric ester salts, polyoxyalkylene alkyl phenyl phosphoric ester salts, and glycerin fatty acid ester monophosphoric ester salts, and the like.

Examples of these salts include alkali metal salts such as a sodium salt and a potassium salt, alkaline earth metal salts such as a magnesium salt, alkanolamine salts such as a monoethanolamine salt, a diethanolamine salt, a triethanolamine salt, and an ammonium salt. Among these salts, an alkali metal salt is preferable.

Among those mentioned above, as the linear alkylbenzene sulfonic acid salts, one having the linear alkyl group having 8 to 20 carbon atoms is preferable, and one having the linear alkyl group having 10 to 14 carbon atoms is more preferable.

As the alkyl sulfuric acid salts, one having a linear or branched alkyl group having 10 to 20 carbon atoms is preferable, and one having a linear or branched alkyl group having 10 to 14 carbon atoms is more preferable.

As the alkyl ether sulfuric acid salts, a polyoxyethylene alkyl ether sulfuric acid salt having a linear or branched alkyl group having 10 to 20 carbon atoms in which 1 to 10 mol of ethylene oxide on average are added thereto is preferable.

As the alkenyl ether sulfuric acid salts, a polyoxyethylene alkenyl ether sulfuric acid salt having a linear or branched alkenyl group having 10 to 20 carbon atoms in which 1 to 10 mol of ethylene oxide on average are added thereto is preferable.

As the alpha-olefin sulfonic acid salts, those having 10 to 20 carbon atoms are preferable, and those having 10 to 14 carbon atoms are more preferable.

As the alkane sulfonic acid salts, a secondary alkane sulfonic acid salt having an alkyl group having 10 to 20 carbon atoms is preferable, and one having an alkyl group having 10 to 14 carbon atoms is preferable.

As the alpha-sulfofatty acid alkyl ester salts, an alpha-sulfofatty acid alkyl ester salt in which the fatty acid residue (the acyl group moiety) has 10 to 20 carbon atoms is preferable. For example, one represented by the formula (2) described below may be preferably mentioned.

As the polyoxyalkylene ether carboxylic acid salts, a polyoxyethylene alkyl ether carboxylic acid salt or a polyoxyethylene alkenyl ether carboxylic acid salt, which has a linear or branched alkyl or alkenyl group having 10 to 20 carbon atoms, and in which 1 to 10 mol of ethylene oxide on average are added thereto is preferable.

In the formula (2), $R^3$ is a hydrocarbon group having 8 to 18 carbon atoms, $R^4$ is a hydrocarbon group having 1 to 6 carbon atoms, and M is a counterion.

The hydrocarbon group of $R^3$ may be linear or branched, or may contain a cyclic structure. The hydrocarbon group of $R^3$ is preferably an aliphatic hydrocarbon group, more preferably a linear or branched alkyl group or a linear or branched alkenyl group, and still more preferably a linear alkyl group or a linear alkenyl group.

The number of carbon atoms of $R^4$ is 1 to 6, and preferably 1 to 3. The hydrocarbon group of $R^4$ may be linear, branched, or may contain a cyclic structure. The hydrocarbon group of $R^4$ is preferably an aliphatic hydrocarbon group, more preferably a linear or branched alkyl group or a linear or branched alkenyl group, and still more preferably a linear alkyl group or a branched chain alkyl group. As $R^4$, a methyl group, an ethyl group, an n-propyl group, an isopropyl group or the like is preferable, and a methyl group, an ethyl group, or an n-propyl group is preferable, and a methyl group is particularly preferable, since detergency is further improved as a cleaning component.

As the counterion of M, one capable of forming a water-soluble salt with $R^3CH(COOR^4)SO_3^-$ is preferable, and examples thereof include an alkali metal ion, a protonated amine, an ammonium ion, and the like. Examples of the alkali metal that can be the counterion include sodium, potassium and the like. Examples of the amine which can be the counterion include primary to tertiary amines, and the like. The total number of carbon atoms of the amine is preferably 1 to 6. The amine may have a hydroxy group. From the viewpoint of increasing the solubility of the alpha-sulfofatty acid alkyl ester salt in water, it is preferable that the amine have a hydroxy group. As an example of the amine having a hydroxy group, an alkanolamine may be mentioned, and the alkanol group preferably has 1 to 3 carbon atoms. Examples of the alkanolamine include monoethanolamine, diethanolamine, triethanolamine and the like.

As M, alkali metal ions are preferable, and sodium ions are particularly preferable in view of availability and in view of easily enhancing the stability of the liquid detergent at low temperature.

As the alpha-sulfofatty acid alkyl ester salt, one obtainable by a known preparation method can be mentioned. For example, as the alpha-sulfofatty acid alkyl ester salt, one obtained by preparing an alpha-sulfofatty acid alkyl ester (alpha-SF acid) by contacting a fatty acid ester as a raw material with sulfuric anhydride or the like, using a tank-type reactor equipped with a stirrer and the like in accordance with a conventional method for sulfonation, and subsequently neutralizing the alpha-SF acid with sodium hydroxide or the like, may be used, or a commercially available product may be used. The alpha-sulfofatty acid alkyl ester salt may be one bleached with hydrogen peroxide or the like before or after neutralization.

From the viewpoint of suppressing soil redeposition with respect to fibers treated (softened) with a softening agent containing a cationic surfactant as an active ingredient, a sulfonic acid salt such as a linear alkylbenzenesulfonic acid salt (LAS), an olefin sulfonic acid salt, an alkanesulfonic acid salt, or an alpha-sulfofatty acid alkyl ester salt (alpha-SF salt), or a sulfuric acid salt such as an alkylsulfuric acid salt, an alkyl ether sulfuric acid salt (AES), or an alkenyl ether sulfuric acid salt is preferable.

Among these sulfonic acid salts or sulfuric acid salts, those having an alkyl group of 10 to 16 carbon atoms are preferable, and LAS having an alkyl group of 10 to 16 carbon atoms, an alpha-olefinsulfonic acid salt having an alkyl group of 10 to 16 carbon atoms, an alpha-SF salt having an alkyl group having 10 to 16 carbon atoms, an alkylsulfuric acid salt having an alkyl group having 10 to 16 carbon atoms, and AES having an alkyl group having 10 to 16 carbon atoms are more preferable. LAS having an alkyl group having 10 to 16 carbon atoms, an alpha-SF salt having an alkyl group having 10 to 16 carbon atoms, or AES having an alkyl group having 10 to 16 carbon atoms is further preferable. Among these, an alpha-SF salt having an alkyl group having 10 to 16 carbon atoms or AES having an alkyl group having 10 to 16 carbon atoms is preferable.

As the component (b), any one type may be used alone, or two or more types thereof may be used in combination.

<Water>

The liquid detergent of the present invention preferably contains water from the viewpoints of ease of handling during production and solubility in water during use.

<Other Components>

In addition to the components (a) and (b), the liquid detergent of the present invention may contain other components ordinarily used in a liquid detergent.

Examples of other components include surfactants other than the components (a) and (b), solvents, hydrotrope agents, chelating agents, bactericides, antiseptics, antifungal agents, pigments, antioxidants, ultraviolet absorbers, perfumes, pH adjusting agents and the like.

Examples of the surfactants other than the aforementioned components (a) and (b) include nonionic surfactants other than the component (a), amphoteric surfactants, and the like.

Examples of the nonionic surfactants other than the component (a) include, for example, a polyoxyalkylene nonionic surfactant in which an alkylene oxide is added to a higher alcohol, an alkylphenol, a higher fatty acid, a higher fatty acid ester, a higher amine or the like (with the proviso that the component (a) is excluded), a polyoxyethylene polyoxypropylene block copolymer, a fatty acid alkanolamide, a polyhydric alcohol fatty acid ester or an alkylene oxide adduct thereof, a fatty acid polyglycerol ester, a sugar fatty acid ester, an alkyl (or alkenyl) amine oxide, an amidoamine oxide, an alkylene oxide adduct of hydrogenated castor oil, an N-alkyl polyhydroxy fatty acid amide, an alkyl glycoside having an alkyl group having 8 or more carbon atoms, and glyceryl ether.

"Higher" as used in the present specification means a compound having 8 or more carbon atoms.

As the nonionic surfactant, a polyoxyalkylene nonionic surfactant is preferable. Among the polyoxyalkylene nonionic surfactants, a polyoxyalkylene alkyl ether (AE) in which an alkylene oxide is added to a saturated higher alcohol is preferable.

Therefore, the nonionic surfactant in the liquid detergent is preferably formed from the component (a) or formed from the component (a) and AE.

Examples of the amphoteric surfactant include amphoteric surfactants such as an alkylbetaine type, an alkylamide betaine type, an imidazoline type, an alkylaminosulfonic acid type, an alkylaminocarboxylic acid type, an alkylamidocarboxylic acid type, an amidoamino acid type, and a phosphoric acid type.

As the surfactant other than the aforementioned components (a) and (b), a nonionic surfactant other than the component (a) is preferable.

Any one of the surfactants other than the aforementioned components (a) and (b) may be used alone, or two or more types thereof may be used in combination.

Examples of the solvent include, for example, an alcohol such as ethanol, 1-propanol, 2-propanol, or 1-butanol, a glycol such as propylene glycol, butylene glycol or hexylene glycol, a polyglycol such as diethylene glycol, triethylene glycol, tetraethylene glycol, polyethylene glycol or dipropylene glycol having a weight average molecular weight ranging from about 200 to 1,000, an alkyl ether such as diethylene glycol monomethyl ether, diethylene glycol monoethyl ether, diethylene glycol monobutyl ether or diethylene glycol dimethyl ether, an aromatic compound such as 2-phenoxyethanol, phenoxy-2-propanol, or benzyl alcohol, and the like.

As the solvent, a solvent other than an aromatic compound is preferable.

As the hydrotropic agent, an aromatic sulfonic acid or a salt thereof can be mentioned. Examples of aromatic sulfonic acids or salts thereof include toluenesulfonic acid, xylenesulfonic acid, cumenesulfonic acid, substituted or unsubstituted naphthalenesulfonic acid, salts thereof, and the like.

Examples of the salt include a sodium salt, a potassium salt, a calcium salt, a magnesium salt, an ammonium salt, an alkanolamine salt, and the like.

The pH adjuster is blended in order to set the pH of the liquid detergent to a desired value. However, when the pH of the liquid detergent can be set to the desired value only by blending the aforementioned components, the pH adjuster may not necessarily be blended.

Examples of the pH adjuster include an acidic compound such as sulfuric acid and hydrochloric acid, and an alkaline compound such as sodium hydroxide and potassium hydroxide. As the alkaline compound, an amine other than the aforementioned alkanol amine can be used. These pH adjusters may be used alone or in combination of two or more types.

<Composition of Liquid Detergent>

The amount of the component (a) contained in the liquid detergent preferably ranges from 3 to 30% by mass, more preferably ranges from 5 to 30% by mass, and still more preferably ranges from 5 to 15% by mass, based on the total mass of the liquid detergent. When the amount of the component (a) is equal to or greater than the above lower limit value mentioned above, the effect of suppressing soil redeposition becomes superior. When the amount of the component (a) is equal to or lower than the upper limit value mentioned above, low-temperature stability of the liquid detergent becomes superior.

The amount of the component (a) contained in the liquid detergent is preferably 7.5% by mass or more, more preferably 12% by mass or more, and still more preferably 100% by mass, with respect to the total mass of the nonionic surfactant. When the amount of the component (a) is equal to or greater than the lower limit value mentioned above, the effect of inhibiting soil redeposition becomes superior.

The amount of the component (b) contained in the liquid detergent preferably ranges from 3 to 30% by mass, more preferably ranges from 5 to 20% by mass, and still more preferably ranges from 5 to 15% by mass, based on the total mass of the liquid detergent. When the amount of the component (b) is equal to or greater than the lower limit mentioned above, the effect of suppressing soil redeposition becomes superior. When the amount of the component (b) is equal to or lower than the upper limit value mentioned above, superior low-temperature stability can be exhibited.

The total amount of the components (a) and (b) contained in the liquid detergent preferably ranges from 5 to 50% by mass, and more preferably ranges from 15 to 30% by mass, based on the total mass of the liquid detergent. When the total amount of the component (a) and the component (b) is equal to or greater than the lower limit mentioned above, the effect of the present invention obtained by using the component (a) and the component (b) in combination can be more easily obtained. When the total content of the component (a) and the component (b) is equal to or lower than the upper limit mentioned above, a degree of freedom of blending of the other components can be easily maintained.

In addition, the total amount of the components (a) and (b) is preferably 10% by mass or more, more preferably 25% by mass or more, and still more preferably 60% by mass or more, and may by 100% by mass, with respect to the total mass of the surfactants. When the total amount of the component (a) and the component (b) based on the total mass of the surfactants is equal to or greater than the aforementioned lower limit value mentioned above, a superior effect of preventing soil redeposition of the liquid detergent and superior low-temperature stability can be exhibited.

The total mass of the surfactants is the sum of the masses of the components (a) and (b) and the surfactants other than the components (a) and (b) (including the case where surfactants other than the components (a) and (b) are not contained).

The mass ratio represented by component (a)/component (b) [the mass ratio of the amount of component (a) to the amount of component (b), hereinafter also referred to as "a/b ratio"] ranges from 0.3 to 10, more preferably ranges from 1 to 5, and still more preferably ranges from 1.5 to 3. When the a/b ratio is within the above range, a superior effect of preventing soil redeposition can be exhibited.

The total amount of the surfactants contained in the liquid detergent preferably ranges from 3 to 50% by mass, more preferably ranges from 5 to 40% by mass, and still more preferably ranges from 10 to 30% by mass, based on the total mass of the liquid detergent. When the total amount of the surfactants is equal to or greater than the lower limit value mentioned above, superior detergency of the liquid detergent can be exhibited. When it is equal to or lower than the upper limit value mentioned above, superior low-temperature stability of the liquid detergent can be exhibited.

The amount of water in the liquid detergent is not particularly limited, but preferably ranges from 40 to 95% by mass, more preferably ranges from 50 to 90% by mass, and still more preferably ranges from 60 to 85% by mass, based on the total mass of the liquid detergent.

The liquid detergent of the present invention preferably has a pH ranging from 5 to 9, and more preferably a pH ranging from 7 to 9, at 25° C. When the pH of the liquid detergent is within the aforementioned preferable range, a good detergency can be easily maintained since when the liquid detergent is preserved for a long time, the component (a) and the alpha-sulfofatty acid alkyl ester salt are more stabilized. In addition, by setting the pH to the upper limit or less, low-temperature stability can be easily enhanced. This is preferable.

In the present invention, the pH of the liquid detergent at 25° C. indicates a value obtained by adjusting a sample at 25° C. and measuring a pH value by means of a pH meter (for example, using the product name "HM-30G" manufactured by DKK-TOA Corporation).

The viscosity of the liquid detergent of the present invention at 25° C. is not particularly limited, but preferably ranges from 10 to 2000 mPa·s, for example. If the viscosity is within the range mentioned above, the liquid detergent can be easily measured with a measuring cap or the like. In addition, if the viscosity is within the range mentioned above, when the liquid detergent is directly applied to the object to be laundered, the liquid detergent can be easily applied thereto.

The viscosity of the liquid detergent in the present specification at 25° C. is a value measured by using a Brookfield viscometer (manufactured by TOKIMEC Co., Ltd.) after adjusting the temperature of the sample to 25° C. (under measurement conditions of, for example, a rotation speed of 30 rpm using a rotor No. 2, the viscosity after rotation for 30 seconds is measured).

The liquid detergent of the present invention can be produced, for example, by dissolving the aforementioned components (a) and (b), and optional components as necessary, in water.

The liquid detergent of the present invention can be used, for example, as a liquid detergent for textile products to be laundered such as clothing materials, a liquid kitchen detergent for washing dishes or vegetables, a liquid detergent for use on a hard surface to be treated such as a toilet, a wall, or a bathroom, or a liquid washer for a human body such as a body soap or a shampoo for cleaning the skin, hair and the like. In particular, the liquid detergent of the present invention is suitably used as a liquid detergent for textile products.

In the liquid detergent of the present invention described above, the aforementioned component (b) is contained together with the aforementioned component (a). For this reason, superior effects of suppressing redeposition of carbon soil and superior cleaning properties are exhibited. In addition, superior stability at low temperature is exhibited, and it is difficult to solidify the liquid detergent or generate precipitates when the liquid detergent is stored under an environment of a low temperature, for example, 10° C. or lower.

The liquid detergent of the present invention contains the aforementioned component (a) and component (b), and the component (b) is preferably an ethylene oxide adduct of a fatty acid methyl ester mixture selected from the group consisting of a fatty acid methyl ester mixture derived from a palm oil-derived fraction having 18 carbon atoms, a fatty acid methyl ester mixture derived from a palm kernel oil-derived fraction having 18 carbon atoms, and a fatty acid methyl ester mixture derived from a coconut oil-derived fraction having 18 carbon atoms.

The liquid detergent of the present invention contains the aforementioned component (a) and component (b), and the component (b) preferably has an alkyl group having 10 to 14 carbon atoms, and in particular, is at least one type selected from the group consisting of an LAS having an alkyl group having 10 to 14 carbon atoms, an alpha-SF salt having an alkyl group having 10 to 14 carbon atoms, and an AES having an alkyl group having 10 to 14 carbon atoms.

The liquid detergent of the present invention contains the aforementioned component (a) and component (b), and a nonionic surfactant other than the component (a), and the anionic surfactant other than the component (a) is preferably AE.

In addition, in the present invention, when a linear alkylbenzene sulfonate (LAS) is contained as the anionic surfactant of the component (b), the amount thereof is preferably suppressed to, for example, 5% by mass or less based on the total mass of the liquid detergent from the viewpoint of effectively suppressing redeposition of carbon soil and further improving the detergency.

EXAMPLES

Hereinafter, the present invention will be described in more detail with reference to examples. It should be understood that the present invention is not limited to these examples. In the examples, "%" indicates "% by mass" unless otherwise specified.

The raw materials used in the present examples are described below.

<Nonionic Surfactant>

Nonion 1: Fatty acid polyoxyethylene methyl ether in which ethylene oxide in an amount of 10 moles on average is added, obtained in Preparation Example 1 described below (ethylene oxide adduct of a fatty acid methyl ester mixture derived from a palm oil-derived C18 fraction; narrow rate 51%).

Nonion 2: Fatty acid polyoxyethylene methyl ether in which ethylene oxide in an amount of 15 moles on average is added, obtained in Preparation Example 2 described below (ethylene oxide adduct of a mixture of C12 and C14 fatty acid methyl esters; narrow rate 33%).

Nonion 3: Fatty acid polyoxyethylene methyl ether in which ethylene oxide in an amount of 10 moles on average is added, obtained in Preparation Example 3 described below (ethylene oxide adduct of C16 saturated fatty acid methyl ester; narrow rate 40%).

Nonion 4: Fatty acid polyoxyethylene methyl ether in which ethylene oxide in an amount of 10 moles on average is added, obtained in Preparation Example 4 described below (ethylene oxide adduct of C18 unsaturated fatty acid methyl ester; narrow rate 51%).

Nonion 5: Fatty acid polyoxyethylene methyl ether in which ethylene oxide in an amount of 10 moles on average is added, obtained in Preparation Example 5 described below (ethylene oxide adduct of a fatty acid methyl ester mixture derived from a palm oil; narrow rate 44%).

AE: Polyoxyethylene alkyl ether having an alkyl group having 12 to 14 carbon atoms in which ethylene oxide in an amount of 9 moles on average is added (LEOX CL-90, trade name, manufactured by Lion Corporation).

<Anionic Surfactant>

LAS: Sodium linear-alkyl (10 to 14 carbon atoms) benzenesulfonate (neutralized product of Lipon LH-200, trade name, manufactured by Lion Corporation, with sodium hydroxide).

AES: Polyoxyethylene alkyl ether sulfate sodium salt having an alkyl group having 12 to 14 carbon atoms in which ethylene oxide in an amount of 2 moles on average is added (EMAL 270N, trade name, manufactured by Kao Corporation).

Alpha-SF salt: PC-48 manufactured by Stepan Co., which is formed from 12/14/16/18 carbon atoms and a mass ratio thereof is about 6/2/1/1.

Preparation Example 1

An alumina-magnesia composite oxide (Kyoward 300, manufactured by Kyowa Chemical Industry Co., Ltd.) having a chemical formula of 2.5 $MgO.Al_2O_3.n\ H_2O$ was calcined for 3 hours at 750° C. under a nitrogen stream. Thereby, a calcined alumina-magnesia composite oxide (Al/Mg molar ratio=0.44/0.56) catalyst was obtained.

In an autoclave with a volume of 4 L, 3.13 g of glycerol and 0.13 g of 40% KOH as a catalyst modifier were placed together with 627 g of a fatty acid methyl ester mixture derived from a palm oil-derived fraction having 18 carbon atoms which having methyl oleate and methyl limoleate as main ingredients (trade name: Pastel M 182, manufactured by Lion Corporation: 69% of methyl oleate, 22% of methyl linoleate, 9% of other fractions having 18 carbon atoms), and 2.5 g of the catalyst obtained by the aforementioned method. Nitrogen substitution was carried out 5 times.

Thereafter, the temperature thereof was raised to 180° C., and the inside of the reaction vessel was returned to atmospheric pressure with nitrogen. In addition, 932 g of ethylene oxide (EO) (corresponding to 10 mol with respect to 1 mol of the mixture) was gradually introduced into the vessel. After the introduction of ethylene oxide (EO) was completed, the pressure which was 0.26 MPa, decreased with the progress of the reaction, and the EO addition reaction was continued for 30 minutes until the pressure became constant at 0.13 MPa. Subsequently, the obtained reaction product was filtered using diatomaceous earth to obtain the target product.

The narrow rate was calculated from the aforementioned mathematical equation (I) by measuring the distribution of ethylene oxide adducts having different mole numbers of added ethylene oxide under the following measurement conditions.

[Measurement Conditions for Distribution of Ethylene Oxide Adducts by HPLC]

Apparatus: LC-6A (manufactured by Shimadzu Corporation).
Detector: SPD-10A,
Measurement wavelength: 220 nm,
Column: Zorbax C8 (manufactured by Du Pont),
Mobile phase: acetonitrile/water=60/40 (volume ratio),
Flow rate: 1 mL/min,
Temperature: 20° C.

Preparation Example 2

The target product was obtained in the same manner as that described in Preparation Example 1, with the exception that a 3:1 (mass ratio) mixture of methyl laurate (a fatty acid methyl ester derived from palm oil-derived fraction having 12 carbon atoms) and methyl myristate (a fatty acid methyl ester derived from palm oil-derived fraction having 14 carbon atoms) (trade name: Pastel M 124, manufactured by Lion Corporation) was used as a raw material, and the addition amount of EO was set to 1,867 g (corresponding to 15 mol based on 1 mol of the mixture).

Preparation Example 3

The target product was obtained in the same manner as that described in Preparation Example 1, with the exception that methyl palmitate (manufactured by Wako Pure Chemical Industries, Ltd., reagent grade 1) was used as a raw material, and the addition amount of EO was set to 1,020 g (corresponding to 10 mol based on 1 mol of methyl palmitate).

Preparation Example 4

In a four-necked flask with a volume of 3 L, equipped with a stirring blade, a condenser and a thermometer, 801.0 g of methanol and 706.2 g of oleic acid (Extraolein 99, manufactured by NOF CORPORATION) (methanol/oleic acid (molar ratio)=10) were placed. 7.5 g of p-toluenesulfonic acid monohydrate (in an amount equivalent to that of p-toluenesulfonic acid monohydrate) as a catalyst was added thereto, subsequently, the temperature of the mixture was raised to 70° C., and the reaction was carried out for 8 hours. After the reaction, 1.6 g of sodium hydroxide (in an amount equivalent to that of p-toluenesulfonic acid monohydrate) was added to deactivate the catalyst. Subsequently, methanol was removed under reduced pressure, and the remaining catalyst was removed by washing with 1 L of water three times using a 3 L separating funnel. Thereafter, the residual water was removed under reduced pressure at 40° C. by a vacuum pump to obtain methyl oleate.

The target product was obtained in the same manner as that described in Preparation Example 1, with the exception that the aforementioned methyl oleate was used as a raw material, and the addition amount of EO was set to 930 g (corresponding to 10 mol with respect to 1 mol of methyl oleate).

Preparation Example 5

The target product was obtained in the same manner as that described in Preparation Example 1, with the exception that a mixture of palm oil-derived fatty acid methyl esters containing methyl palmitate, methyl oleate, and methyl linoleate as main components (PALM METHYL ESTER C18 ME-50, manufactured by CALOTINO Corporation: palmitic acid 40%—methyl oleate 41%—methyl linoleate 13%—other components 6%) was used as a raw material, and the addition amount of EO was set to 932 g (corresponding to 10 mol based on 1 mol of the mixture).

Examples 1 to 21 and Comparative Examples 1 to 7

In accordance with the compositions shown in the following Tables 1 to 3, nonionic surfactants and anionic surfactants were added to water, and mixed, and thereby, liquid detergents according to Examples 1 to 21 and Comparative Example 1 to 6 were obtained. In addition, a liquid detergent of Comparative Example 7 was obtained in the same manner as that described above with the exception that no anionic surfactant was added.

The composition (blending components, and amount (%)) of the liquid detergent of each of the examples obtained is shown in Tables 1 to 3 below. In the following Tables 1 to 3, a blank in the components means that there is no blended component. The amount of the blending component indicates the pure amount. "Balance" indicated in the amount of purified water means the remaining amount to be added so that the total blending amount (%) of all components contained in the liquid detergent becomes 100%. The ratio of the unsaturated fatty acid residue and the ratio of the polyunsaturated fatty acid residue respectively indicate an average value in the total of the fatty acid polyoxyethylene alkyl ethers in which the fatty acid residues have 16 to 18 carbon atoms, among the nonionic surfactants contained in the liquid detergent.

With respect to the liquid detergent of each example, the effects of suppressing soil redeposition and low-temperature stability were evaluated as shown below.

a. The evaluation results are shown in Tables 1 to 3 below.
<Effects of Suppressing Soil Redeposition>
Preparation of Test Cloth As a white cloth (test cloth) for use in soil-transferring of carbon particles, a cotton underwear (manufactured by Fujibou Apparel Corporation, B. V. D. GOLD round neck short-sleeved underwear, made of 100% cotton) cut into a square (5 cm in length×5 cm in width) was used.

"Soil Redeposition Experiment 1"

As a carbon for use in evaluation of soil transferring of carbon particles, surface-modified acetylene black (wet surface-treated carbon black, manufactured by Daito Kasei Kogyo Co., Ltd.) was used.

A soil redeposition experiment was carried out by using a Terg-O-tometer (manufactured by UNITED STATES TESTING Corp.), and washing for 10 minutes at 25° C. in a total concentration of the nonionic surfactant and the anionic surfactant of 200 ppm, at a bath ratio of 30 (4.5 g of white cloth+25.5 g of balanced cotton cloth) and at a carbon particle concentration of 100 ppm. After completion thereof, the soil-transferred white cloth was dried with an iron.

The reflectivity of the white cloth before and after the soil redeposition experiment was measured using a color-difference meter (spectroscopic type color-difference meter SE 2000, manufactured by Nippon Denshoku Industries Co., Ltd.), and Z values were calculated. ΔZ1 corresponding to a value obtained by subtracting the Z value after the soil redeposition experiment from the Z value before the soil redeposition experiment was obtained, and was indicated as "Effect 1 of suppressing soil redeposition" in Tables 1 to 3 shown below. For each of 5 pieces of white cloth, the aforementioned ΔZ1 was obtained, and the average value thereof was calculated therefrom and was used as ΔZ1 of the liquid detergent. The aforementioned ΔZ1 indicates the degree of darkening due to the soil redeposition experiment. As the ΔZ1 is decreased, a superior effect of suppressing soil redeposition is obtained.

"Soil Redeposition Experiment 2"

As a carbon for use in evaluation of soil transferring of carbon particles, an environmental standard sample NIES CRM No. 28 city air dust was used by assuming PM 2.5 derived from air pollution. A soil redeposition experiment was carried out by using a Terg-O-tometer (manufactured by UNITED STATES TESTING Corp.), and washing for 10 minutes at 25° C. in the total concentration of the nonionic surfactant and the anionic surfactant of 50 ppm, at a bath ratio of 30 and at a city air dust (PM 2.5) concentration of 100 ppm. After completion thereof, the soil-transferred white cloth was dried with an iron.

Subsequently, the reflectivity of the white cloth before and after the soil redeposition experiment was measured using a color-difference meter (spectroscopic type color-difference meter SE 2000, manufactured by Nippon Denshoku Industries Co., Ltd.), and Z values were calculated. ΔZ2 corresponding to a value obtained by subtracting the Z value after the soil redeposition experiment from the Z value before the soil redeposition experiment was obtained, and was indicated as "Effect 2 of suppressing soil redeposition" in Tables 1 to 3 shown below. For each of 5 white cloths, the aforementioned ΔZ2 was obtained, and the average value thereof was calculated therefrom and was used as ΔZ2 of the liquid detergent. The aforementioned ΔZ2 indicates the degree of darkening due to the soil redeposition experiment. As the ΔZ2 is decreased, a superior effect of suppressing soil redeposition is obtained.

"Evaluation of Detergency"

A soil-deposited cloth by the city air dust (PM2.5) was prepared (soil deposition step) by using a Terg-O-tometer (manufactured by UNITED STATES TESTING Corp.), and stirring a cloth with the aforementioned city air dust (PM 2.5) at a concentration of 150 ppm at a bath ratio of 30 in tap water for 30 minutes, and then by dehydrating and drying the cloth. Subsequently, the cloth was washed for 10 minutes at 25° C. in the total concentration of the nonionic surfactant and the anionic surfactant of 50 ppm, at a bath ratio of 30 (5 pieces of the cloth polluted with PM 2.5+balanced cotton cloth), rinsed for 3 minutes, and dehydrated. After completion thereof, the washed cloth which had been soil-deposited by city air dust (PM 2.5) was dried with an iron (washing step). The series of treatments of the aforementioned soil deposition step to washing step was repeated twice.

Subsequently, the detergency (%) of the washed cloth which had been soil-deposited by city air dust (PM 2.5) was obtained using the color-difference meter (spectroscopic type color-difference meter SE 2000, manufactured by Nippon Denshoku Industries Co., Ltd.), by means of the Kubelka-Munk equation expressed by the following mathematical equation (II), and was shown in Tables 1 to 3 below. The following mathematical equation (II) is composed of two equations, wherein R is the reflectance measured using a colorimeter Σ-9000 manufactured by Nippon Denshoku Co., Ltd. The detergency was evaluated by the average value obtained from those of five pieces of the test cloth.

Detergency (%) =
$100 \times (K/S \text{ of soil-deposited cloth} - K/S \text{ of cleaned cloth})/$
$(K/S \text{ of soil-deposited cloth} - K/S \text{ of standard cloth})$ $$K/S = \frac{\left(1 - \frac{R}{100}\right) \times 2}{\frac{2R}{100}} \quad \text{(II)}$$

<Low-Temperature Stability>

1 g of a liquid detergent was placed in a test tube and stored for 1 day at −20° C. to completely solidify. Subsequently, the detergent was placed in a thermostatic chamber at −5° C., and the temperature was raised by 1° C. per hour. The temperature at which the entire detergent was completely dissolved and became transparent was visually judged. As the aforementioned temperature is reduced, low-temperature stability becomes superior.

TABLE 1

| | | Comparative Example 1 | Example 1 | Example 2 | Example 3 | Example 4 | Comparative Example 2 | Example 5 | Example 6 | Comparative Example 3 | Example 7 | Comparative Example 4 |
|---|---|---|---|---|---|---|---|---|---|---|---|---|
| Nonionic surfactant | Nonion 1 (C18) | | 3 | 5 | 10 | 15 | | 5 | 15 | | 5 | |
| | Nonion 2 (C12,14) | | | | | | | | | 15 | 10 | |
| | Nonion 3 (C16) | | | | | | | | | | | |
| | Nonion 4 (C18) | | | | | | | | | | | |
| | Nonion 5 (whole) | | | | | | | | | | | |
| | AE | 15 | 12 | 10 | 5 | | 15 | 10 | | | | 15 |
| Anionic surfactant | LAS | 5 | 5 | 5 | 5 | 10 | | | | 5 | 5 | |
| | AES | | | | | | 5 | 5 | 5 | | | |
| | MES (124) | | | | | | | | | | | 5 |
| | Water | balance | balance | balance | balance | balance | balance | balance | balance | balance | balance | balance |
| (a) | Rate of unsaturated fatty acid residue (%) | 0 | 91 | 91 | 91 | 91 | 0 | 91 | 91 | 0 | 91 | 0 |
| | Rate of polyunsaturated fatty acid | 0 | 24 | 24 | 24 | 24 | 0 | 24 | 24 | 0 | 24 | 0 |

TABLE 1-continued

|  |  | Comparative Example 1 | Example 1 | Example 2 | Example 3 | Example 4 | Comparative Example 2 | Example 5 | Example 6 | Comparative Example 3 | Example 7 | Comparative Example 4 |
|---|---|---|---|---|---|---|---|---|---|---|---|---|
| Evaluation | residue (%) Effect 1 of suppressing soil redeposition | 50 | 41 | 34 | 31 | 30 | 51 | 33 | 34 | 52 | 34 | 51 |
|  | Effect 2 of suppressing soil redeposition | 6 | 4 | 3 | 2 | 2 | 6 | 3 | 2 | 6 | 3 | 5 |
|  | Detergency (%) | 33 | 40 | 40 | 43 | 42 | 36 | 41 | 45 | 35 | 41 | 34 |
|  | Low-temperature stability | 2° C. or less | 2° C. or less | 2° C. or less | 2° C. or less | 2° C. or less | 2° C. or less | 2° C. or less | 2° C. or less | 2° C. or less | 2° C. or less | 2° C. or less |

TABLE 2

|  |  | Example 8 | Example 9 | Example 10 | Example 11 | Example 12 | Comparative Example 5 | Example 13 | Comparative Example 6 | Comparative Example 7 |
|---|---|---|---|---|---|---|---|---|---|---|
| Nonionic surfactant | Nonion 1 (C18) | 15 |  |  | 9 | 7.5 | 7 | 3 | 2 | 10 |
|  | Nonion 2 (C12,14) |  | 12 |  |  |  |  |  |  |  |
|  | Nonion 3 (C16) |  |  |  | 6 | 7.5 | 8 |  |  |  |
|  | Nonion 4 (C18) |  |  |  |  |  |  | 12 | 13 |  |
|  | Nonion 5 (whole) |  | 3 | 3 |  |  |  |  |  |  |
|  | AE |  |  | 12 |  |  |  |  |  | 5 |
| Anionic surfactant | LAS |  | 5 | 5 | 5 | 5 | 5 | 5 | 5 |  |
|  | AES |  |  |  |  |  |  |  |  |  |
|  | MES (124) | 5 |  |  |  |  |  |  |  |  |
|  | Water | balance | balance | balance | balance | balance | balance | balance | balance | balance |
| (a) | Rate of unsaturated fatty acid residue (%) | 91 | 55 | 55 | 55 | 46 | 42 | 98 | 99 | 91 |
|  | Rate of polyunsaturated fatty acid residue (%) | 24 | 24 | 24 | 24 | 24 | 24 | 4 | 3 | 24 |
| Evaluation | Effect 1 of suppressing soil redeposition | 32 | 43 | 42 | 32 | 33 | 34 | 28 | 29 | 53 |
|  | Effect 2 of suppressing soil redeposition | 2 | 4 | 4 | 2 | 2 | 2 | 2 | 2 | 4 |
|  | Detergency (%) | 48 | 40 | 41 | 49 | 48 | 46 | 47 | 47 | 42 |
|  | Low-temperature stability | 2° C. or less | 14° C. | 14° C. | 14° C. | 15° C. | 16° C. or more | 2° C. or less | 16° C. or more | 2° C. or less |

TABLE 3

|  |  | Example 13 | Example 14 | Example 15 | Example 16 | Example 17 | Example 18 | Example 19 | Example 20 | Example 21 |
|---|---|---|---|---|---|---|---|---|---|---|
| Nonionic surfactant | Nonion 1 (C18) | 20 | 27 | 34 | 20 | 27 | 34 | 20 | 27 | 34 |
|  | Nonion 2 (C12,14) |  |  |  |  |  |  |  |  |  |
|  | Nonion 3 (C16) |  |  |  |  |  |  |  |  |  |
|  | Nonion 4 (C18) |  |  |  |  |  |  |  |  |  |
|  | Nonion 5 (whole) |  |  |  |  |  |  |  |  |  |
|  | AE |  |  |  |  |  |  |  |  |  |
| Anionic surfactant | LAS | 10 | 13 | 16 |  |  |  | 5 | 7 | 8 |
|  | AES |  |  |  | 10 | 13 | 16 | 5 | 6 | 8 |
|  | MES (124) |  |  |  |  |  |  |  |  |  |
| Optional component | Ethanol | 8 | 12 | 14 | 8 | 14 | 18 | 8 | 14 | 16 |
|  | Water | balance | balance | balance | balance | balance | balance | balance | balance | balance |
| (a) | Rate of unsaturated fatty acid residue (%) | 91 | 91 | 91 | 91 | 91 | 91 | 91 | 91 | 91 |
|  | Rate of polyunsaturated fatty acid residue (%) | 24 | 24 | 24 | 24 | 24 | 24 | 24 | 24 | 24 |
| Evaluation | Effect 1 of suppressing soil redeposition | 34 | 34 | 35 | 30 | 31 | 31 | 32 | 32 | 34 |
|  | Effect 2 of suppressing soil redeposition | 3 | 2 | 2 | 2 | 2 | 2 | 3 | 2 | 2 |
|  | Detergency (%) | 40 | 42 | 43 | 44 | 46 | 47 | 43 | 46 | 46 |
|  | Low-temperature stability | 2° C. or less | 10° C. | 12° C. | 2° C. or less | 10° C. | 14° C. | 2° C. or less | 10° C. | 14° C. |

As shown in Tables 1 to 3, in the liquid detergents of Examples 1 to 21, all the $\Delta Z1$ values were 43 or less, all the $\Delta Z2$ values were 4 or less, and superior effects of suppressing soil redeposition were exhibited. In addition, in the liquid detergents of Examples 1 to 21, all the detergency (%) were 40% or more, superior detergency was exhibited, and good low-temperature stability was exhibited.

On the other hand, in the liquid detergents of Comparative Examples 1, 2, and 4 containing no component (a), in the liquid detergent of Comparative Example 3 using the fatty acid polyoxyethylene alkyl ether having fatty acid residues with 12 and 14 carbon atoms in place of the component (a), and in the liquid detergent of Comparative Example 7 containing no component (b), inferior effects of suppressing soil redeposition were exhibited.

In the liquid detergent of Comparative Example 5 having a rate of an unsaturated fatty acid residue of component (a) of less than 45%, and in the liquid detergent of Comparative Example 6 having a rate of a polyunsaturated fatty acid residue of component (a) of less than 4%, inferior low-temperature stability was exhibited.

What is claimed is:

1. A liquid detergent comprising:
component (a): a nonionic surfactant which contains compounds represented by the following formula (1) wherein an average value of m in said formula (1) ranges from 5 to 20; and in which a ratio of the compound of formula (1) wherein $R^1$ is a double bond-containing unsaturated hydrocarbon group is equal to or greater than 45% by mass with respect to a total amount of the component (a), and a ratio of the compound wherein $R^1$ is an unsaturated hydrocarbon group having two or more double bonds is equal to or greater than 4% by mass with respect to a total amount of the compounds wherein $R^1$ is an unsaturated hydrocarbon group; and
component (b): an anionic surfactant, $$R^1CO(EO)_mOR^2 \tag{1}$$

wherein $R^1$ is a saturated or unsaturated hydrocarbon group having 15 to 17 carbon atoms; EO is an oxyethylene group; m is a positive integer; and $R^2$ is an alkyl group having 1 to 3 carbon atoms.

* * * * *